United States Patent
Baynham et al.

(10) Patent No.: US 7,468,069 B2
(45) Date of Patent: Dec. 23, 2008

(54) STATIC ANTERIOR CERVICAL PLATE (75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 492 days.

(21) Appl. No.: 10/776,731

(22) Filed: Feb. 10, 2004

(65) Prior Publication Data
US 2005/0177161 A1 Aug. 11, 2005

(51) Int. Cl.
*A61B 17/80* (2006.01)
(52) U.S. Cl. ........................... 606/296; 606/280
(58) Field of Classification Search ............ 606/61, 606/69, 70, 71, 73; 623/17.11
See application file for complete search history.

(56) References Cited

U.S. PATENT DOCUMENTS

| | | |
|---|---|---|
| 74,489 A | 2/1868 | Bidwel |
| 434,503 A | 8/1890 | Corry |
| 556,642 A | 3/1896 | Ressing |
| 824,867 A | 7/1906 | Houghton |
| 872,897 A | 12/1907 | Chapman et al. |
| 951,800 A | 3/1910 | Center |
| 1,084,680 A | 1/1914 | Wegener |
| 1,105,105 A | 7/1914 | Sherman |
| 1,907,506 A | 5/1933 | Coburn |
| 1,980,336 A | 11/1934 | Hoagland |
| 2,423,511 A | 7/1947 | Luben et al. |
| 2,757,457 A | 8/1956 | Ziegelski, Sr. |
| 3,100,516 A | 8/1963 | Nabb |
| 3,244,170 A | 4/1966 | McElvenny |
| 3,386,437 A | 6/1968 | Treace |
| 3,604,414 A | 9/1971 | Borges |
| 3,709,219 A | 1/1973 | Halloran |
| 3,741,205 A | 6/1973 | Markoff et al. |
| 3,750,652 A | 8/1973 | Sherwin |
| 3,840,014 A | 10/1974 | Ling et al. |
| RE28,841 E | 6/1976 | Allgower et al. |
| 3,960,147 A | 6/1976 | Murray |
| 4,003,376 A | 1/1977 | McKay et al. |
| 4,037,980 A | 7/1977 | Haentjens |
| 4,069,586 A | 1/1978 | Skelton |
| 4,102,339 A | 7/1978 | Weber et al. |
| 4,113,227 A | 9/1978 | Cigliano |
| 4,338,926 A | 7/1982 | Kummer et al. |
| 4,388,921 A | 6/1983 | Sutter et al. |
| RE31,628 E | 7/1984 | Allgower et al. |
| 4,484,570 A | 11/1984 | Sutter et al. |
| 4,488,543 A | 12/1984 | Tornier |
| 4,493,317 A | 1/1985 | Klaue |

(Continued)

*Primary Examiner*—Eduardo C Robert
*Assistant Examiner*—David Comstock
(74) *Attorney, Agent, or Firm*—McHale & Slavin, P.A.

(57) ABSTRACT

A bone plate for use in anterior cervical spinal fixation has interlocking components to prevent dislodgement of the plate due to anatomical forces. The plate is formed in the shape of a block letter C and the exposed surface is smooth to prevent trauma to internal body tissue. The plate spans the intervertebral space with each end attached to an adjacent vertebrae by bone screws threadably engaged with the bone. The distal ends of the bone screws The plate has a screw lock in each end for preventing the locking screws from backing out.

16 Claims, 6 Drawing Sheets

U.S. PATENT DOCUMENTS

| | | | |
|---|---|---|---|
| 4,503,848 A | 3/1985 | Caspar et al. | |
| 4,542,539 A | 9/1985 | Rowe, Jr. et al. | |
| 4,651,724 A | 3/1987 | Berentey et al. | |
| 4,733,657 A | 3/1988 | Kluger | |
| 4,762,122 A | 8/1988 | Slocum | |
| 4,771,767 A * | 9/1988 | Steffee | 606/61 |
| 4,794,918 A | 1/1989 | Wolter | |
| 4,896,661 A | 1/1990 | Bogert et al. | |
| 4,898,161 A | 2/1990 | Grundei | |
| 4,943,292 A | 7/1990 | Foux | |
| 4,957,495 A | 9/1990 | Kluger | |
| 4,959,065 A | 9/1990 | Arnett et al. | |
| 5,000,166 A | 3/1991 | Karpf | |
| 5,002,544 A | 3/1991 | Klaue et al. | |
| 5,019,079 A | 5/1991 | Ross | |
| 5,041,113 A | 8/1991 | Biedermann et al. | |
| 5,052,373 A | 10/1991 | Michelson | |
| 5,053,036 A | 10/1991 | Perren et al. | |
| 5,057,111 A | 10/1991 | Park | |
| 5,059,194 A | 10/1991 | Michelson | |
| 5,085,660 A | 2/1992 | Lin | |
| 5,108,395 A | 4/1992 | Laurain | |
| 5,127,912 A | 7/1992 | Ray et al. | |
| 5,127,914 A | 7/1992 | Calderale et al. | |
| 5,129,899 A | 7/1992 | Small et al. | |
| 5,147,361 A | 9/1992 | Ojima et al. | |
| 5,151,103 A | 9/1992 | Tepic et al. | |
| 5,167,662 A | 12/1992 | Hayes et al. | |
| 5,180,381 A | 1/1993 | Aust et al. | |
| 5,190,544 A | 3/1993 | Chapman et al. | |
| 5,209,751 A | 5/1993 | Farris et al. | |
| 5,217,497 A | 6/1993 | Mehdian | |
| 5,234,430 A | 8/1993 | Huebner | |
| 5,300,073 A | 4/1994 | Ray et al. | |
| 5,338,197 A | 8/1994 | Kwan | |
| 5,364,399 A | 11/1994 | Lowery et al. | |
| 5,380,328 A | 1/1995 | Morgan | |
| 5,397,363 A | 3/1995 | Gelbard | |
| 5,423,826 A * | 6/1995 | Coates et al. | 606/96 |
| 5,456,685 A | 10/1995 | Huebner | |
| 5,478,340 A | 12/1995 | Kluger | |
| 5,478,348 A | 12/1995 | Bajada | |
| 5,492,442 A | 2/1996 | Lasner | |
| 5,520,690 A | 5/1996 | Errico et al. | |
| 5,527,314 A | 6/1996 | Brumfield et al. | |
| 5,531,554 A | 7/1996 | Jeanson et al. | |
| 5,531,746 A | 7/1996 | Errico et al. | |
| 5,545,163 A | 8/1996 | Miller et al. | |
| 5,545,165 A | 8/1996 | Biedermann et al. | |
| 5,549,612 A | 8/1996 | Yapp et al. | |
| 5,558,674 A | 9/1996 | Heggeness et al. | |
| 5,562,663 A | 10/1996 | Wisnewski et al. | |
| 5,562,672 A | 10/1996 | Huebner et al. | |
| 5,578,034 A | 11/1996 | Estes | |
| 5,601,553 A | 2/1997 | Trebing et al. | |
| 5,603,713 A | 2/1997 | Aust et al. | |
| 5,607,426 A | 3/1997 | Ralph et al. | |
| 5,616,142 A | 4/1997 | Yuan et al. | |
| 5,616,144 A | 4/1997 | Yapp et al. | |
| 5,643,265 A | 7/1997 | Errico et al. | |
| 5,662,652 A | 9/1997 | Schafer et al. | |
| 5,672,175 A | 9/1997 | Martin | |
| 5,676,666 A | 10/1997 | Oxland et al. | |
| 5,676,703 A | 10/1997 | Gelbard | |
| 5,735,853 A | 4/1998 | Olerud | |
| 5,735,899 A | 4/1998 | Schwartz et al. | |
| 5,755,796 A | 5/1998 | Ibo et al. | |
| 5,766,254 A | 6/1998 | Gelbard | |
| D402,032 S | 12/1998 | Stone | |
| 5,849,012 A | 12/1998 | Abboudi | |
| D406,646 S | 3/1999 | Stone | |
| 5,876,402 A | 3/1999 | Errico et al. | |
| 5,876,446 A | 3/1999 | Agrawal et al. | |
| 5,954,722 A | 9/1999 | Bono | |
| 5,984,925 A * | 11/1999 | Apgar | 606/69 |
| 6,022,350 A | 2/2000 | Ganem | |
| 6,030,389 A | 2/2000 | Wagner et al. | |
| 6,139,550 A | 10/2000 | Michelson | |
| 6,152,927 A | 11/2000 | Farris et al. | |
| 6,224,602 B1 | 5/2001 | Hayes | |
| 6,231,610 B1 | 5/2001 | Geisler | |
| 6,342,055 B1 | 1/2002 | Eisermann et al. | |
| 6,379,354 B1 * | 4/2002 | Rogozinski | 606/61 |
| 6,398,783 B1 | 6/2002 | Michelson | |
| 6,436,142 B1 | 8/2002 | Paes et al. | |
| 6,454,771 B1 | 9/2002 | Michelson | |
| 6,585,738 B1 * | 7/2003 | Mangione et al. | 606/61 |
| 6,602,255 B1 | 8/2003 | Campbell et al. | |
| 6,652,525 B1 | 11/2003 | Assaker et al. | |
| 6,669,700 B1 | 12/2003 | Farris et al. | |
| 6,695,846 B2 | 2/2004 | Richelsoph et al. | |
| 6,730,127 B2 | 5/2004 | Michelson | |
| 6,740,088 B1 | 5/2004 | Kozak et al. | |
| 6,936,051 B2 | 8/2005 | Michelson | |
| 2004/0102773 A1 | 5/2004 | Morrison et al. | |

* cited by examiner

STATIC ANTERIOR CERVICAL PLATE

FIELD OF THE INVENTION

This invention relates to the field of orthopedic surgery and, more particularly, to spinal fixation.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma. The bone plate of this invention is useful in all these situations.

The interface between the bone screws and the bone presents problems of stability and long term usage that have been addressed in different ways. One of the major problems is usually termed as back-out. This defines the condition in which the screws attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contributes greatly to the problem.

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface.

Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

What is needed in the art is a bone plate that provides improved visualization of the vertebral interspace for graft placement, improved ability to align and position the plate, and tapped bone screws for better purchase.

SUMMARY OF THE INVENTION

Disclosed is a bone plate for use in anterior cervical spinal fixation. The bone plate has interlocking components to prevent dislodgement of the plate due to anatomical forces. The bone plate is C-shaped with a smooth exposed surface to prevent trauma to internal body tissue. The plate spans the intervertebral space with each end attached to an adjacent vertebrae by bone screws threadably engaged with tubular bone anchors. The plate has a screw lock in each end for preventing the bone screws from backing out.

It is an objective of this invention to provide a bone plate, suitable for anterior cervical fixation, having countersunk screw holes, a low profile in cross section allowing the bone plate to be countersunk into the bone and a smooth distal surface to reduce the possibility of traumatizing adjacent soft tissue during use.

Another objective of this invention is to provide a reduced width in the central portion of the bone plate for visualizing the intervertebral space below the proximal surface of the plate.

A further objective of the invention is to provide bone screws with a fluted leading end to provide a tapped bore in the bone for better purchase.

Another objective of the invention is to provide bone screws extending through the countersunk screw holes into the bone with the leading ends of the screws formed as a tap.

Yet another objective of the invention is to provide a bone plate with a sliding screw lock blocking back out of the bone screws.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

The bone plate system 10 may be made from any materials having requisite strength and being suitable for use in the body. One complete bone plate system is shown in FIG. 1 and FIG. 2 though it is understood that several different sizes of interchangeable components may be supplied together as a kit for mixing and matching components to size a system for a particular patient. A kit may have several different sized bone screws 11 varying in diameter and length. The different sized locking screws may have the same sized heads 13 to be used in different sized bone plates 14 with screw holes and larger countersunk depressions 15 of a complementary size. There may be several different sized screw locks 16 to fit into the different sized screw lock slots 17. The kit merely refers to the dissembled components that can be assembled to produce an integral whole which corresponds to the anatomical features of a particular patient.

The bone plate 14 is shaped in the form of a block letter C with a vertical staff 18 connected at each end to arms 19 and 20 extending normal to the staff. Each of the arms 19 and 20 contain two countersunk screw holes. The reduced width of the bone plate, in the area between the arms, permits a clear visualization of the intervetrebral space during the fitting and placement of the plate.

Each of the arms 19 and 20 contains a screw lock slot 17 located between the countersunk depressions 15 surrounding the screw holes. The screw lock slot 17 extends through each arm and communicates with the countersunk depressions 15 through slits 24 in the sidewalls of the countersunk depression.

The bone plate system 10 addresses the problem of backout by providing several locking features in the connection of the plate 14 with the bone. These locking features all resist the biomechanical loads placed on the implanted system and result in an aggregate resistance to movement of the components.

Figure 3:
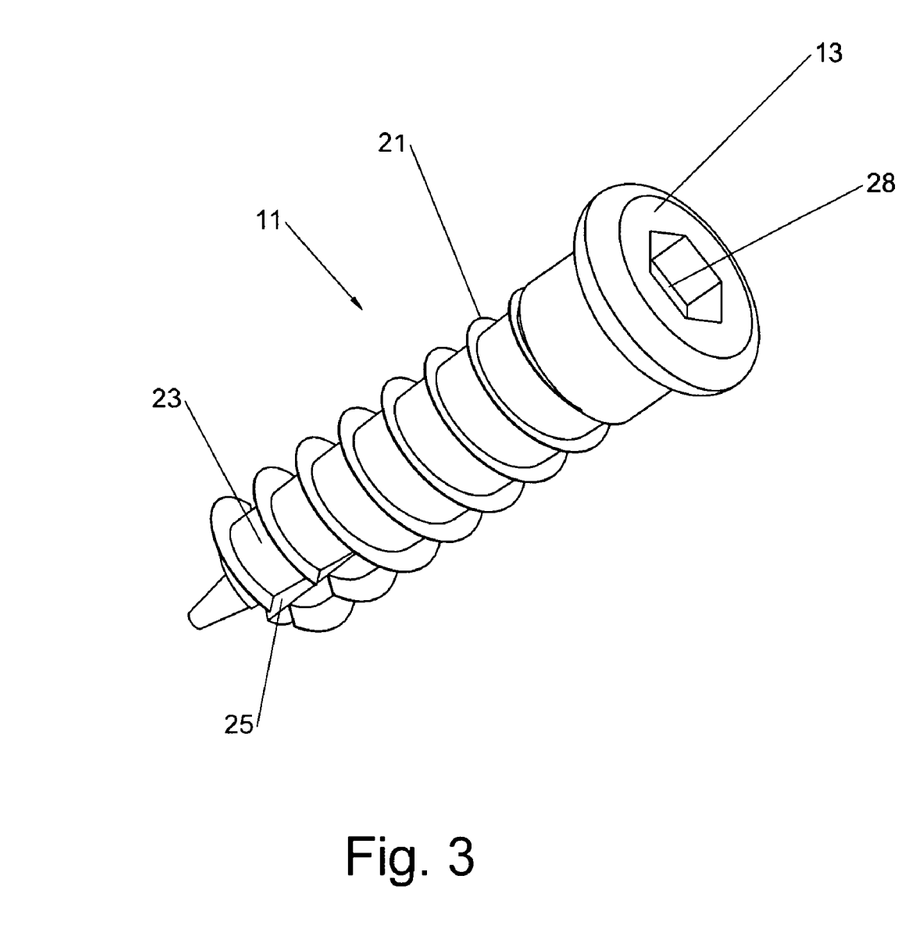
FIG. 3 is a perspective of the bone screw of this invention.

The bone screws 11 are initially inserted into the bone through pilot holes drilled in the bone or by the use of guide wires. The plate 14 may be used as a guide to align the longitudinal axis of the bone screws with the longitudinal axis of the countersunk screw holes 15' in the plate. The bone screws 11 are driven into the bone with a tool (not shown) that engages the slots 28 for rotation. The exterior screw threads 21 draw the screw into its seated position in the bone. However, the screw threads 21 produce a mirror image of the toroidal ramp at the bone interface which is a path of least resistance in the opposite direction. The leading or proximal end of the screw 11 has a number of flutes 25 in the side wall dividing the proximal circumference into segments 26. Further, the leading end is tapered toward a smaller end. This tap structure of the leading end of the bone screws 11 produces a cutting or sweeping function in the bone-screw interface by collecting debris as the screw is inserted to provide a smooth bore in the bone for the following threads.

Once the bone screws 11 are extended through the screw holes of the bone plate 14 with the threads 21 threadably engaging the interior of the smooth bone bore, the locking screws are rotated by a tool (not shown) fitted into the receptacle 28. As shown, the bone screw 11 has a smooth unthreaded shank near the head 13. The leading end of the screw has a tapered portion 23 to engage the leading end of a pilot hole in the bone. The bone screw heads 13 are surrounded by the depressions 15 and compressively disposed against the bottoms of the depressions. Therefore, the screw 11 is locked in place by a smooth new bone-anchor interface and the screw threads engage the walls of the bore. Of course, other combinations of locking screws and anchor configurations may be used, such as, a constant taper of each.

Figure 1A:
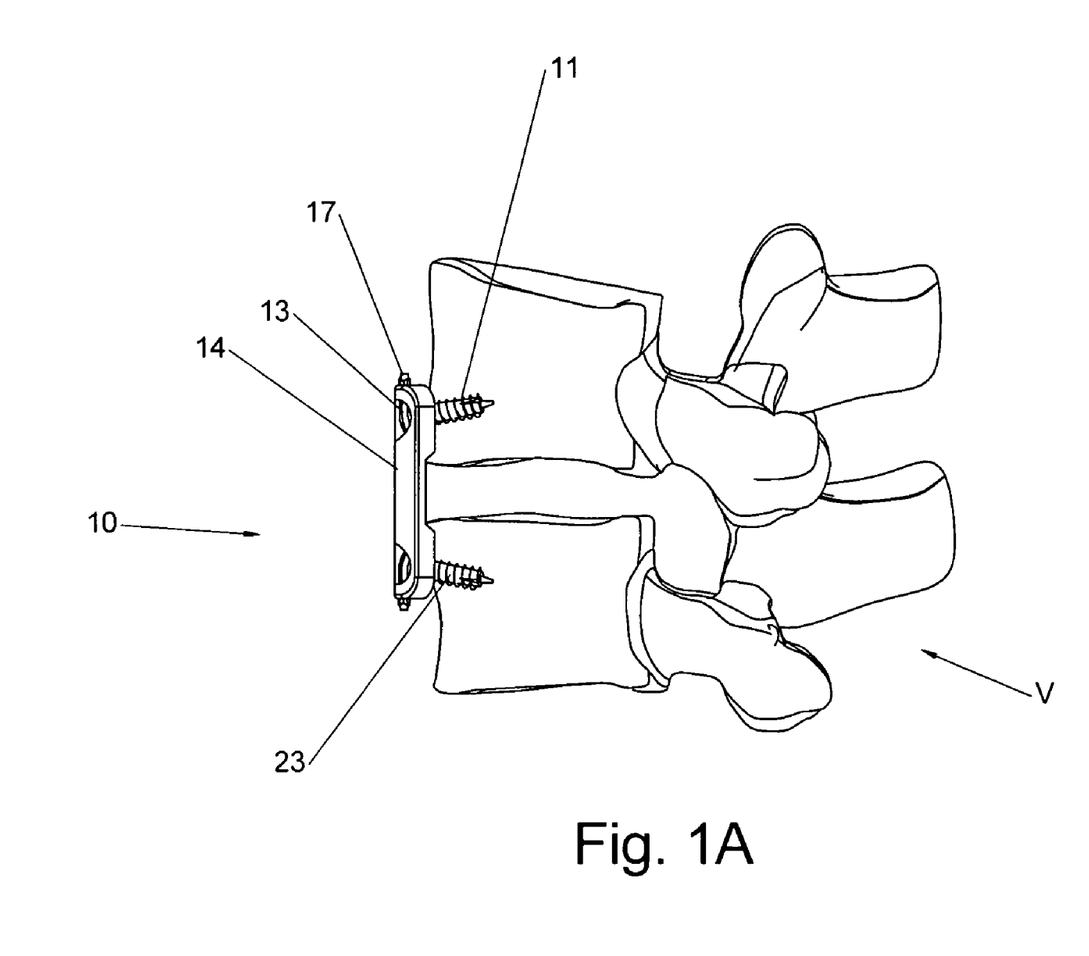
FIG. 1 is a side view, partially in section, of the plate of this invention implanted in the spine.
Figure 1B:
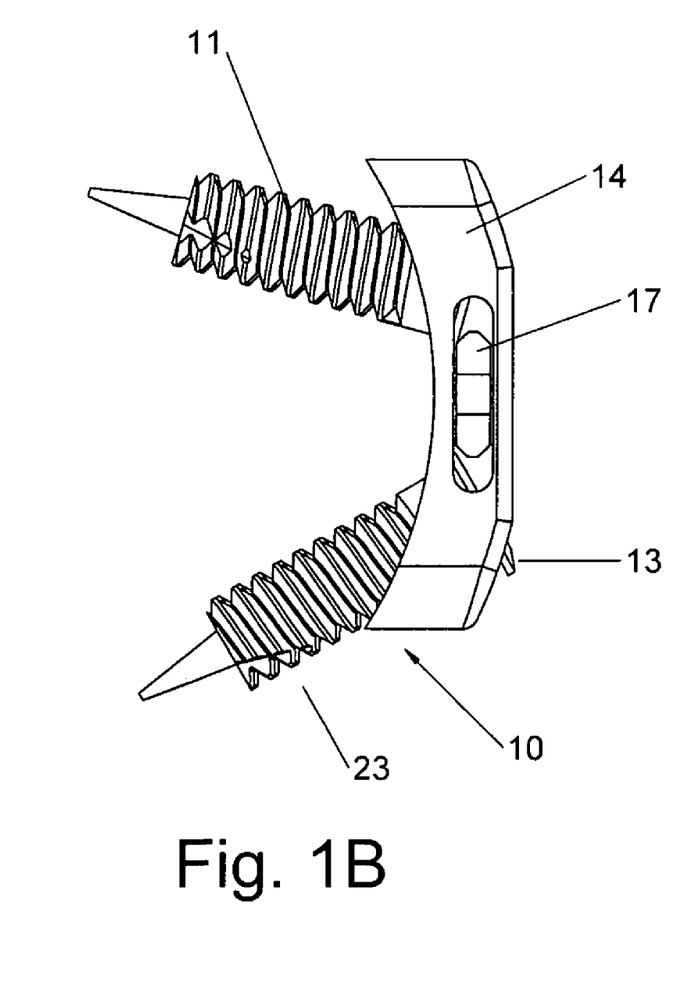
Figure 2:
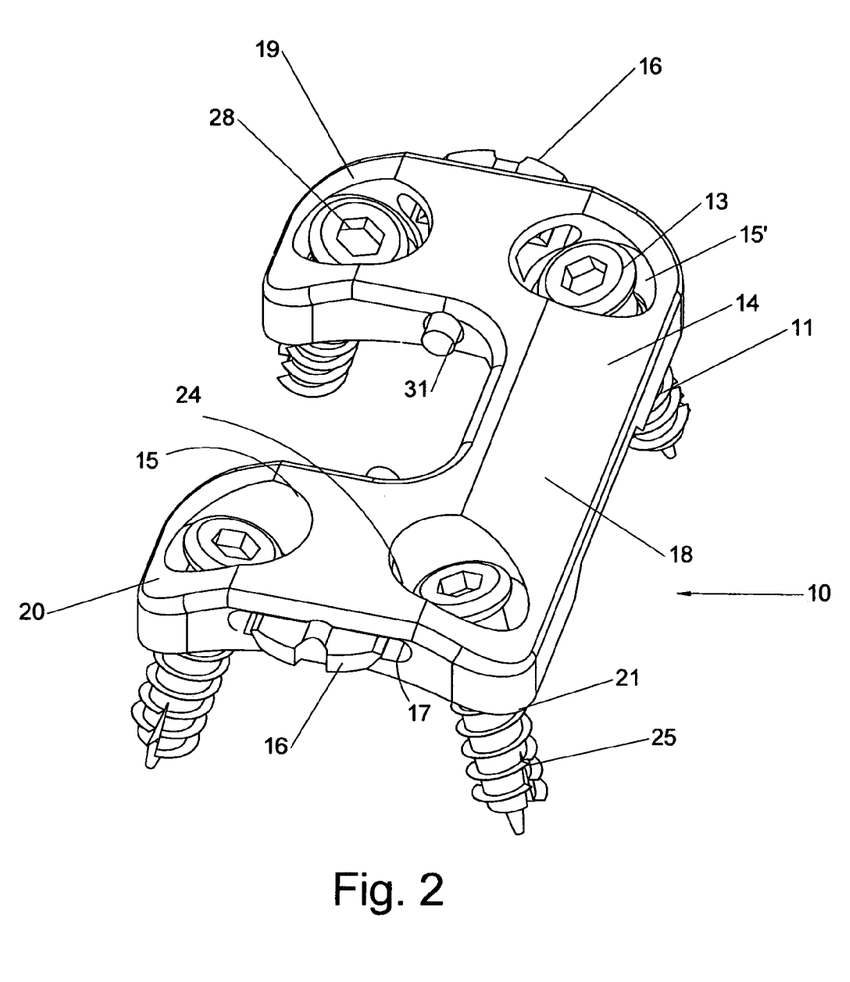
FIG. 2 is a perspective of assembled bone plate system of this invention.

The anterior surface of the vertebrae V and the plate 10 form a low profile interface, as shown in FIG. 1A. This is especially important in reducing the possibility of internal trauma to adjacent soft tissue, e.g., in the anterior cervical spinal fixation. The plate is curved to further conform the plate to the anatomy and reduce the silhouette. FIG. 1B illustrates the plate set forth in FIG. 1A which is rotated 90 degrees and shown without a pictorial of the vertebrae.

Figure 4:
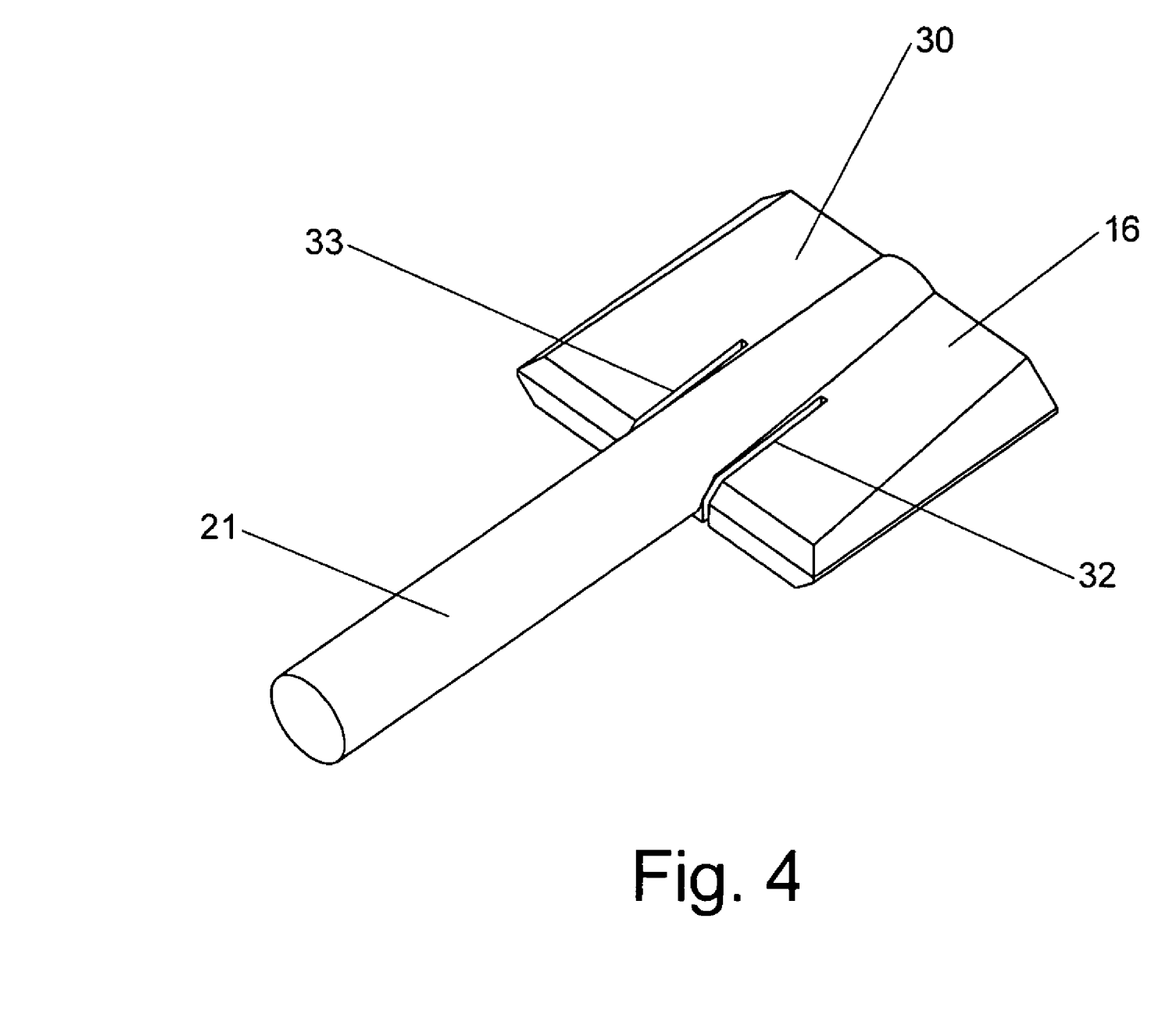
FIG. 4 is a perspective of the screw lock.
Figure 5:
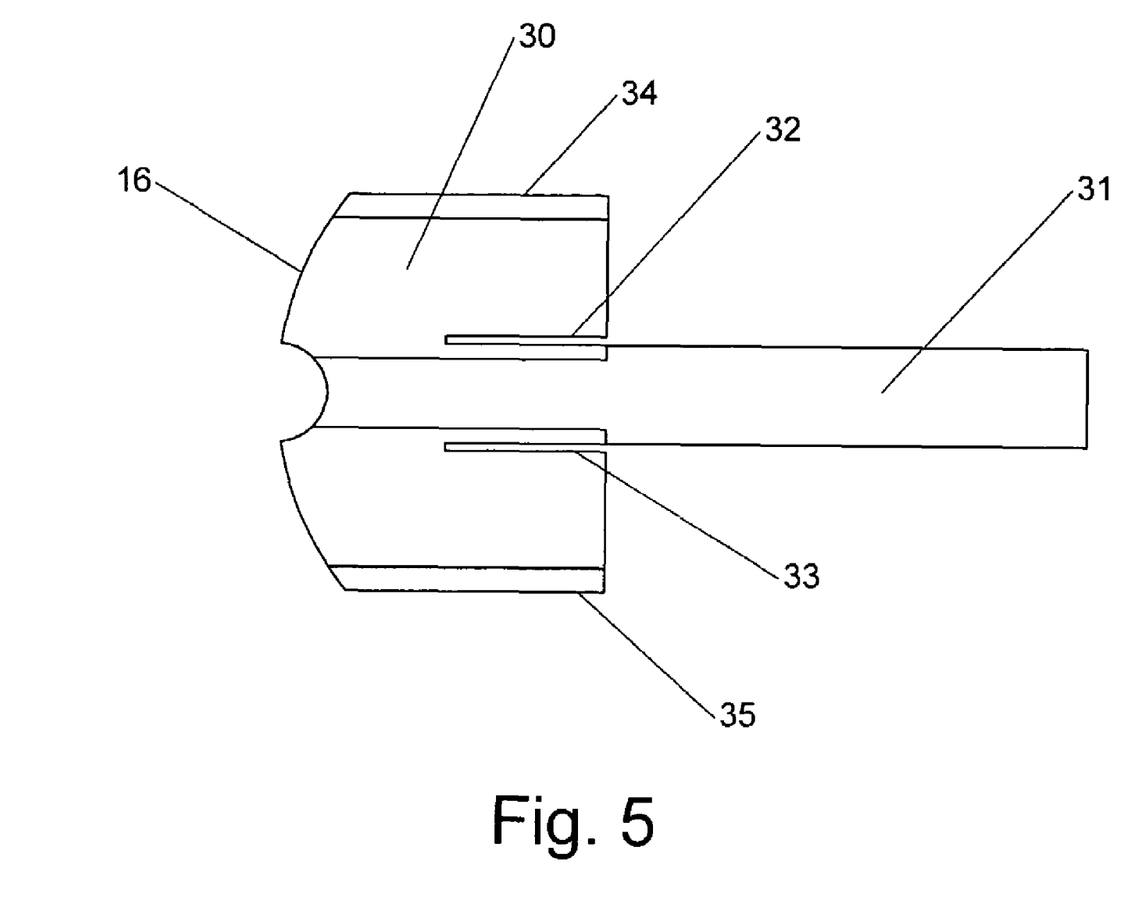
FIG. 5 is a top plan view of the screw lock.

After the screws 11 have been seated in the depressions 15, the screw lock 16 is placed in the screw lock slot 17 formed in the plate 14. The screw lock 16 has a substantially flat elongated body 30 with a narrow central extension 31 on one end. The extension 31 is located between two longitudinal slots 32 and 33 formed in the body 30. The slots 32 and 33 provide some resilience to the shape of the body 30 to maintain the screw lock 16 in the screw lock slot 17. The longitudinal edges of the body are preferably thinned at 34 and 35 to allow the screw lock 17 to slide over the screw heads 13. In one embodiment, the screw lock 16 may be tapered from a larger thickness opposite the central extension 31 to wedge into slot 17 as the screw lock is inserted into the slot.

The assembly is completed by sliding the screw locks 16 through the arms 19 and 20 with the thinned edges 34 and 35 of the body 30 extending through the slits 24 to forcibly engage the screw heads 13. The forces produced by the frictional contact of the screw lock with the screw lock slot and the screw heads firmly wedges the screw lock in place and prevents the lock screws from backing out.

The implanted bone plate system results in a positive lock at the proximal ends of the bone anchors and locking screws and an additional lock at the distal end of the locking screws. If the plate must be removed, at some later date, forceps may be applied to the extension 31 and the arms 19 and 20 to force the screw lock from the screw lock slot.

What is claimed is:

1. An implant for stabilizing skeletal bone across a discontinuity comprising a plate having a first end and a second end with an intermediate length to span a discontinuity and a width to accommodate at least one screw hole in each of said first end and said second end, the width of said intermediate length being less than said width of said first end and said second end, said plate including a thickness with a proximal surface for contacting a bone and an opposite distal surface, said plurality of screw holes extending through said thickness for accepting bone screws, said plurality of screw holes each having an enlarged depression in said distal surface, each said depression having a continuous sidewall connected to a bottom wall between said proximal and said distal surfaces, each said screw hole and each said depression having a longitudinal axis, a plurality of bone screws with external threads adapted to penetrate said plurality of screw holes, said bone screws each having an enlarged heads adapted to engage said bottom of each said depressions whereby said bone screws are inserted through said plate and adapted to threadably engage said bone to stabilize the bone across the discontinuity whereby said discontinuity may be observed through said intermediate length during implantation and, said first and second end each contain a slot, each said slot forming a cavity having a thickness length and width, wherein each said length and width are defined by substantially planar upper and lower surfaces, said upper and lower surfaces being substantially parallel to said proximal and distal surfaces, said distal surface extending completely over and enclosing said cavity, the dimension of said thickness of each said slot being less than the dimension of said length of each said slot, and the dimension of said thickness of each said slot being less than the dimension of said width of each said slot, each of said slots extending through said sidewall of each of said depressions, a screw lock slidably disposed in each of said slots whereby said screw lock may be slid into said depressions to prevent back out of said bone screws.

2. An implant of claim 1 wherein said longitudinal axis of each said screw hole and each depression on said first end diverges from said longitudinal axis of each said screw hole on the first end and each said screw hole and each said depression on said second end diverges from said longitudinal axis of each said screw hole on the second end.

3. An implant of claim 2 wherein each said plurality of bone screws has one internal diameter, said plurality of bone screws each have a fluted proximal end.

4. An implant of claim 3 wherein said longitudinal axis of each said screw hole and each depression on said one end diverges from said longitudinal axis of each said screw hole and each said depression on said second end.

5. An implant of claim 4 wherein said first end and said second end each have a slot between said proximal and said distal surfaces, each of said slots extending through said sidewall of each of said depressions, a screw lock slidably disposed in each of said slots whereby said screw lock may be slid into said depressions to prevent back out.

6. An implant of claim 5 wherein said first end and said second end each have at least two screw holes.

7. An implant of claim 3 wherein said first end and said second end each have a slot between said proximal and said distal surfaces, each of said slots extending through said sidewall of each of said depressions, a screw lock slidably disposed in each of said slots whereby said screw lock may be slid into said depressions to prevent back out.

8. An implant of claim 2 wherein said first end and said second end each have a slot between said proximal and said distal surfaces, each of said slots extending through said sidewall of each of said depressions, a screw lock slidably disposed in each of said slots whereby said screw lock may be slid into said depressions to prevent back out.

9. An implant of claim 1 wherein said slot in said first end and said second end extends through a side wall formed between said proximal and distal surfaces of said first end and said second end, said screw lock is in the form of an elongated body with a narrow central extension formed between two longitudinal slots, said extension passing through said side wall whereby said screw lock may be removed.

10. An implant of claim 1 wherein said first end and said second end each have at least two screw holes.

11. A spinal stabilization system for an anterior cervical fixation of two adjacent vertebrae comprising a rigid plate having a first end, a second end and an intermediate length to span the intervertebral space, said first end and said second end each having a width, said intermediate length having a lesser width, said intermediate length asymmetrically connected to said first end and said second end, said rigid plate having a proximal surface for contact with vertebrae and an opposite distal surface, a plurality of screw holes in said first end and a plurality of screw holes in said second end, each of said plurality of screw holes countersunk with a depression, said depression having a continuous side wall connected to a bottom between said proximal surface and said distal surface, a plurality of bone screws engaging said screw holes, said bone screws having an enlarged head engaging said bottom, said first end and said second end each have a slot between said proximal and said distal surfaces, said slot in the first end and said slot in the second end each forming a cavity having a thickness length and width, wherein each said length and width are defined by substantially planar upper and lower surfaces, said upper and lower surfaces being substantially parallel to said proximal and distal surfaces, said distal surface extending completely over and enclosing said cavity, the dimension of said thickness of each said slot being less than the dimension of said length of each said slot, and the dimension of said thickness of each said slot being less than the dimension of said width of each said slot, each of said slots extending through said sidewall of each of said depressions, a screw lock slidably disposed in each of said slots whereby said screw lock may be slid into said depressions to contact said bone screw heads whereby said locking screws are prevented from backing-out of said plate.

12. A spinal stabilization system of claim 11 wherein said plurality of screw holes and each said depressions have a longitudinal axis through said plate, said longitudinal axis of said plurality of screw holes on said first end diverging from said longitudinal axis of one another said longitudinal axis of said plurality of screw holes on said second end diverging from said longitudinal axis of one another.

13. A spinal stabilization system of claim 11 wherein a plurality of bone screws each have a leading end and a distal end, said leading end having flutes.

14. A spinal stabilization system of claim 11 wherein said plurality of bone screws each have a leading end and a distal end, said leading end being reduced in diameter, said exterior threads adapted to engage a vertebra.

15. A spinal stabilization system of claim 11 wherein said slot in said first end and said second end extends through a side wall formed between said proximal and distal surfaces of said first end and said second end, said screw lock is in the form of an elongated body with a narrow central extension formed between two longitudinal slots, said extension passing through said side wall of said first end and said second end, whereby said screw lock may be removed.

16. A spinal stabilization system of claim 11 wherein said plate is curved to reduce the silhouette.

* * * * *